United States Patent [19]

Shepherd et al.

[11] Patent Number: 4,812,574

[45] Date of Patent: Mar. 14, 1989

[54] PROCESS FOR PREPARING THIAZOLOBENZIMIDAZOLES AND INTERMEDIATES USED THEREIN

[75] Inventors: Robin G. Shepherd, Windsor, England; Sie-Yearl Chai, Collegeville, Pa.; Maynard E. Lichty; Arnold S. Milowsky, both of Coatesville, Pa.

[73] Assignees: John Wyeth & Brother Ltd., Maidenhead, England; American Home Products Corporation, New York, N.Y.

[21] Appl. No.: 133,823

[22] Filed: Dec. 23, 1987

[30] Foreign Application Priority Data

Jan. 21, 1987 [GB] United Kingdom ............... 8701228

[51] Int. Cl.$^4$ ............................................. C07D 513/04
[52] U.S. Cl. ................................... 548/151; 548/149
[58] Field of Search .............................. 548/151, 154

[56] References Cited

U.S. PATENT DOCUMENTS 4,214,089  7/1980  Fenichel et al. ................... 548/151
4,361,574  11/1982  Grant et al. ......................... 548/151

FOREIGN PATENT DOCUMENTS 1262292  2/1972  France .
1380507  1/1975  France .

OTHER PUBLICATIONS

Abstract—J. Med. Chem., 1976, vol. 19, No. 4m, S. C. Bell & P. H. L. Wei.
Weygand, Preparative Organic Chemistry, pp. 813–819, (1972).
March, Advanced Organic Chemistry, pp. 901–903, (1985).
Maulding, J. Pharm. Sci., 66, 1175, (1977).

Primary Examiner—Robert Gerstl
Attorney, Agent, or Firm—George Tarnowski

[57] ABSTRACT

The invention concerns a process for preparing a thiazolo[3,2-a]benzimidazole of formula I

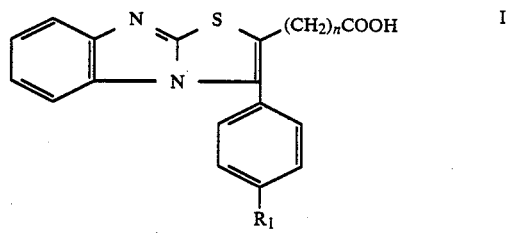

in which formula n is 1 or 2, and $R_1$ is hydrogen, lower alkyl, lower alkoxy, trifluoromethyl or halo, or a salt thereof which comprises dehydrating a compound of formula II,

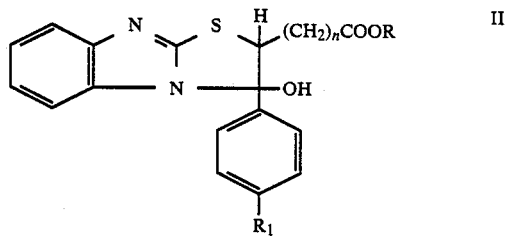

or a salt thereof wherein n and R, are as defined above, and COOR is an acid or ester function in the presence of an acid selected from sulphuric, sulphonic and phosphoric acid or mixtures thereof and if desired or required an inert solvent provided that if water is present then the amount of water is less than about 15% by volume of the acid, the reaction being carried out with heating if necessary.

10 Claims, No Drawings

PROCESS FOR PREPARING THIAZOLOBENZIMIDAZOLES AND INTERMEDIATES USED THEREIN

This invention relates to a process for the preparation of pharmacologically active thiazolobenzimidazoles and to the intermediates used therein. More particularly this invention relates to a process for the preparation of thiazolo[3,2-a]benzimidazoles and to furo[2′,3′:4,5]-thiazolo[3,2-a]benzimidazolone intermediates formed in said process.

Thiazolo[3,2-a]benzimidazoles are disclosed in U.S. Pat. No. 4,214,089, published 22 July 1980, as antineoplastic agents and/or as enhancers of the immune response. Many other compounds possess the ability to inhibit growth of neoplastic tissue, however, cytotoxicity is a major side effect injuring other tissues in the body. These thiazolo-[3,2-a]benzimidazoles are noted for their low incidence of side effects, particularly their low thyrotoxic liability. One of the compounds exemplified and claimed therein has the name 3-(p-chlorophenyl)thiazolo[3,2-a]benzimidazole-2-acetic acid. This compound and related thiazolo[3,2-a]benzimidazoles are also disclosed in U.S. Pat. No. 4,361,574 published 30 Nov. 1982, as inhibitors of mammalian collagenase. Collagen is a major organic component of the surface tissue of the cornea, skin, gastrointestinal viscera, joint mucosa and other areas of the body. Collagenases are capable of breaking down collagen; thereby destroying collagen-based tissue which constitutes the major organic component of the areas previously noted. Hence collagen inhibitors are useful in the treatment of diseases where destruction of collagen connective tissue plays a central role, such as for example periodontal disease, rheumatoid arthritis corneal ulcerations and so forth. In U.S. Pat. Nos. 4,214,089 and 4,361,574 the process for preparing the thiazolo[3,2-a]-benzimidazoles described involves the dehydration of a corresponding 2,3-dihydro-3-hydroxy-thiazolo[3,2-a]benzimidazole by warming at reflux temperature in an aqueous acid, dioxane mixture.

Accordingly the reaction may be represented by the scheme below:

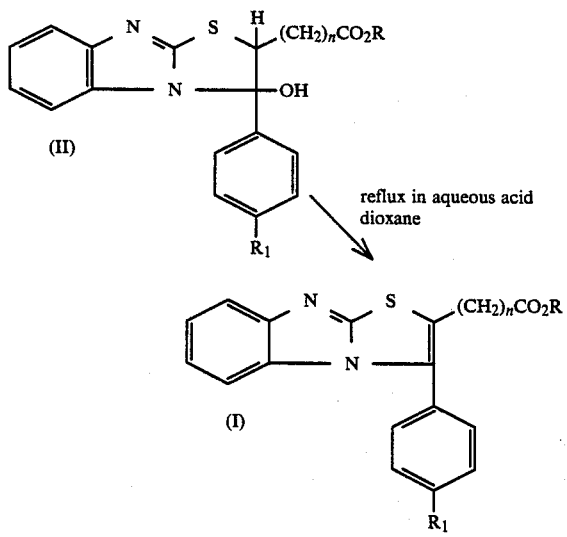

in which formulae n is 1 or 2, R is hydrogen or lower alkyl and $R_1$ is hydrogen, lower alkyl, lower alkoxy, trifluoromethyl or halo. In the case of 3-(p-chlorophenyl)thiazolo[3,2-a]benzimidazole itself, Example 1 of U.S. Pat. No. 4,361,574 illustrates the preparation in only 42% yield using 6N HCl and dioxane as solvent and heating at reflux for 18 hours. Indeed it has been found that this process for preparing compounds of formula I gives relatively poor yields ranging from 20 to 50 percent and furthermore the reaction product is difficult to purify without a further significant loss in yield. The yield for this same process as described in Journal of Medicinal Chemistry, 1976, Vol, 19, No.4. pps 524–530 is only 23%.

It has now surprisingly been found that by carrying out the reaction, with heating if necessary, in the presence of a strong acid selected from the group consisting of sulphuric, sulphonic and phosphoric acids or mixtures thereof then the yield of the aforementioned reaction may be substantially improved and a cleaner product obtained.

Accordingly this invention provides a process for preparing thiazolo[3,2-a]benzimidazoles of formula I as defined above or a salt thereof wherein R˙ is hydrogen which comprises dehydrating a compound of formula II as defined above wherein COOR is an acid or ester function in the presence of acid selected from the group consisting of sulphuric, sulphonic and phosphoric acids or mixtures thereof and if desired or required an inert solvent provided that if water is present then the amount of water is less than about 15% by volume of the acid, the reaction being carried out with heating if necessary.

If the reaction is carried out using a liquid acid then solvent is not required but can be present. However for sulphonic acids which are solid at reaction temperatures then an inert solvent is used. Examples of suitable solvents for solid sulphonic acids are haloalkanes, e.g. dichloromethane or chloroform. Examples of sulphonic acids are aliphatic or aromatic-sulphonic acids such as alkane- or aryl-sulphonic acids, especially where the alkane has 1 or 6 carbons and the aryl has 6 to 10, most preferably methane- or ethane-sulphonic acid. Examples of arylsulphonic acids are benzene- or p-toluenesulphonic acid. A halosulphonic acid may also be used, e.g. chlorosulphonic acid.

It is most preferred to carry out the reaction under substantially anhydrous conditions but small amounts of water may be present e.g. up to about 15% v/v based on acid. Preferably the amount is not more than about 10% by volume based on acid, most preferably less than about 5% v/v. When sulphuric acid is used it is preferred to have some water present to prevent charring; e.g. up to about 4% v/v based on acid. The reaction is conveniently carried out at room temperature and for a sufficient time to achieve optimum product yield. For example when concentrated sulphuric acid is used reaction times of 3–5 hours and reaction temperatures of from 5° to 25° C. provide high yields (e.g. 95±5%) of product. It has been found that the ratio of compound of formula II to acid affects reaction times being favoured by excess quantities of acid. For example by changing the ratio of reactants reaction times may be between a few minutes up to 24 hours or longer. Typically the ratio of acid to compound of formula II is within a range from about 12:1 to about 0.3:1 volume by weight, e.g. from about 10:1 to about 0.5:1. Reaction times may be shortened by applying heat to the reaction mixture. Inert solvents may be employed in the reaction but generally reaction temperature and or reaction times must be raised to achieve optimum yields to compensate. Examples of inert solvents are alkanoic acids e.g. acetic acid. Since the reaction can proceed without heating it provides a substantial saving in energy costs over the previously disclosed route. A further important advantage is that product yield can be virtually quantitative as may be seen from the Examples herein.

The starting materials of formula II and methods for making them are also disclosed in U.S. Pat. No. 3,704,239. Other ester analogues may be prepared by analogous processes. Preferably R is hydrogen or lower alkyl.

In the course of investigating the process of this invention it was surprisingly found that an intermediate lactone of tetracyclic structure was formed during the reaction. It was observed that the intermediate lactone could be isolated in good yield from the reaction mixture if the reaction was not allowed to run its full course through to the compound of formula I. Anhydrous conditions are preferred for lactone formation. The intermediates have the formula shown below:

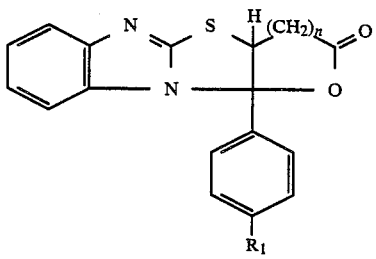

III wherein n and $R_1$ have the meanings above. Preferably n is 1.

Accordingly in a second aspect this invention provides lactones of formula III as defined above. The existence of the intermediate of formula III is even more surprising in view of the teaching of Bell et al in J.Med.-Chem. (ibid) where conditions for producing lactones gave a rearranged product instead of a lactone.

In detail Bell et al found that whereas certain diazolothiazoleacetic acids could be cyclised by acetic anhydride to give the corresponding lactone derivatives, compounds of formula II under the same conditions rearranged instead to give a cyclic thiazinone. They suggest that the difference in behaviour is caused by electronic effects due to the presence of the benzo ring. Accordingly it is surprising that lactones of formula III not only can be formed as disclosed herein but also are stable and can be isolated.

Accordingly in a further aspect this invention provides a process for preparing a lactone of formula III which comprises cyclising a compound of formula II as defined above in the presence of sulphuric acid or a sulphonic acid or mixtures thereof and if desired or required an inert solvent. Preferred acids and solvents for forming the intermediate lactone are the same as those for forming the final product of formula I. Substantially anhydrous conditions are preferred. When it is desired to convert a compound of formula II as defined above to a compound of formula I then the intermediate lactone need not be isolated but merely formed in situ. However, since the intermediate lactone can be isolated yet a further aspect of this invention is a process for preparing a compound of formula I as defined above wherein R is hydrogen which comprises acidifying a lactone of formula III as defined above with an acid preferably selected from sulphuric, sulphonic or phosphoric acid or mixtures thereof if desired in the presence of water in an amount up to about 15% by volume of the acid. Preferably the reaction is carried out under substantially anhydrous conditions (i.e up to about 5% by volume of water based on acid) and if desired in the presence of an inert solvent. Preferably the acid is a liquid sulphonic acid or a sulphonic acid (e.g. p-toluenesulphonic acid) in the presence of an inert solvent such as dichloromethane.

The following Examples illustrate this invention:

Example 1

3-(p-Chlorophenyl)thiazolo[3,2-a]benzimidazol-2-acetic acid

A mixture of 100 g of 3-(p-Chlorophenyl)-2,3,-dihydro-3-hydroxythiazolo[3,2-a]benzimidazol-2-acetic acid, hydrobromide and 200 ml of methanesulphonic acid was stirred overnight in a 500 ml round bottom flask. Thin layer chromatography on silica plates (solvent ethyl acetate/acetic acid) indicated rapid formation of an intermediate. After 20 hours at room temperature thin layer chromatography (silica plates, ethyl acetate/acetic acid) showed the presence of a single component. The mixture was poured into water and the resulting crystals removed by filtration. The crystalline product was suspended in 5 volumes of hot water for ½ hour, filtered and the procedure repeated. After a final aqueous wash the material was dried in vacuo to yield the title compound (75 g, 91%) m.p. 242°-3° C.

Analysis

Found: C, 59.87; H, 3.21; N, 8.37%

$C_{17}H_{11}ClN_2O_2S$ requires C, 59.57; H, 3.23; N, 8.17%.

Example 2

10a-(4-Chlorophenyl)-3a,10a-Dihydrofuro(2',3':4,5)-Thiazolo[3,2-a]benzimidazol-2(3H)-one A mixture of 10 g of 3-(p-chlorophenyl)-2,3-dihydro-3hydroxythiazole[3,2-a]benzimidazol-2-acetic acid, hydrobromide and 20 ml methanesulphonic acid was stirred for 5 minutes at room temperature in a 150 ml round bottom flask. The mixture was diluted with methylene dichloride (100 ml) and washed successively with water, sodium bicarbonate solution and water. The organic phase was dried by evaporation and the residue recrystallised from diisopropyl ether to give the title compound, mp 115°-7° C.

Analysis

Found: C, 59.96; H, 3.17; N, 7.96%

$C_{17}H_{11}ClN_2O_2S$ requires C, 59.96; H, 3.23; N, 8.17%.

Example 3

3-(p-Chlorophenyl)thiazolo[3,2-a]benzimidazol-2-acetic acid

The product of Example 2 (5 g) is stirred overnight in 10 mls. of methanesulphonic acid to give the title compound identical to the product of Example 1, mp 242°-243° C.

Example 4

3-(p-Chlorophenyl)thiazolo[3,2-a]benzimidazole-2-acetic acid

A solution of sulphuric acid (4.0 l) was cooled to 5° C. then 3-(p-chlorophenyl)-2,3,-dihydro-3-hydroxythiazolo[3,2-a]benzimidazole-2-acetic acid hydrochloride salt (1.66 kg, 4.18 mol.) was added portionwise over one hour maintaining a temperature range of 15°–20° C. The mixture was stirred for an additional three hours at 25° C.

Water (6.0 l) was heated to 45° C. and the reaction mixture added to it over forty-five minutes maintaining a temperature range of 55°–60° C. The mixture was stirred for thirty minutes at 55°–60° C. and then cooled to 35° C. The sulphate salt of 3-(p-chlorophenyl)-thiazolo[3,2-a]benzimidazole-2-acetic acid was isolated by centrifugation and washed with water (6.0 l). The filter cake was spun down for fifteen minutes.

The wet sulphate was combined with water (10.0 l), heated to 60° C. and stirred for one hour. The slurry was cooled to 35° C. and the crude product isolated by centrifugation. The solids were washed with water (5.0 l) and the filtercake spun down for fifteen minutes.

The wet filtercake was combined with water (10.5 l) and stirred at 20°–25° C. while basifying to a pH of about 9.5 with concentrated ammonium hydroxide (0.4 l). The solution was stirred for fifteen minutes before line filtering through a 0.2μ line filter. The residual solids were rinsed with water (1.0 l).

The product solution was acidified over a twenty minute period to a pH of 5.5 at 20°–25° C. by adding glacial acetic acid (0.380 l). The slurry was stirred for thirty minutes. The title compound was isolated by centrifugation, washed with water (4.0 L), spun down for 30 minutes and dried in a forced air oven at 55°–60° C. A yield of 1334 g or 93% of theory was obtained, mp 242°–244° C.

| | |
|---|---|
| HPLC Assay: | 99.6% |
| Non Acidic Titration: | 99.8% |
| Total Impurities: | 0.02% |

EXAMPLE 5

3-(p-Chlorophenyl)thiazolo[3,2-a]benzimidazole-2-acetic acid

Concentrated sulphuric acid (200 ml) was cooled to 0° C., and to it was added portionwise a total of 100 g of 3-(p-chlorophenyl)-2,3-dihydro-3-hydroxythiazolo[3,2-a]benzimidazole-2-acetic acid, hydrobromic acid salt keeping the temperature of the reaction mixture under 10° C. After all was added , the resulting dark red solution was stirred until the temperature of the reaction mixture reached 25° C. The solution was then stirred for 3 hours at 25° C. until the colour of the solution became a light yellow.

The light yellow solution was added dropwise to 300 ml of hot water (50° C.) so as not to exceed the temperature over 60° C.

After the addition was complete the mixture was stirred at 60° C. for 1 hour. White solids were collected by filtration at 60° C., reslurried in 550 ml of hot water (60° C.) and stirred for 30 minutes at 60° C. The solids were removed by filtration at 60° C. and washed with water (200 ml).

To the solids in H$_2$O (500 ml), with stirring was added 19 ml of concentrated ammonium hydroxide to make the pH of the solution 9.5. The solution was filtered through a bed of celite. to the clear filtrate, glacial acetic acid (20 ml) was added dropwise until pH 5.5. The precipitate was stirred for 1 hour, collected by filtration and washed twice with water (200 mL). The title compound was dried under vacuum at 60° C. for 18 hours, 68.9 g, mp 242°–244° C.

Analysis

C$_{17}$H$_{11}$ClSO$_2$ requires: C,59.56; H,3.24; N,8.17;
Found: C-59.48; H,3.46; N,8.08%.

EXAMPLE 6

3-(p-Chlorophenyl)thiazolo[3,2-a]benzimidazole-2-acetic acid

To 40 ml of 85% phosphoric acid, 20 g of 3-(p-chloro-phenyl)-2,3-dihydro-3-hydroxythiazolo[3,2-a]benzimidazole-2-acetic acid, hydrochloric acid salt was added portionwise. After the addition was complete, the mixture was heated to 100° C. and stirred for 5 hours at 100° C. The reaction solution was then cooled to 25° C. and added dropwise to 100 ml of hot water (50° C.) so as not to exceed a temperature of 60° C. After the addition was complete, the mixture was stirred at 60° C. for 1 hour. Off white solids were collected by filtration at 60° C., reslurried in 80 ml of hot water (60° C.) and stirred for 30 minutes at 60° C. The off white solids were removed by filtration and washed with 50 ml of H$_2$O. To the solids in 75 ml of H$_2$O was added 8.2 ml ammonium hydroxide to make pH of the solution 9.5. The solution was filtered through a bed of celite. To the clear solution, 4 ml of glacial acetic acid was added dropwise until pH 5.5. The precipitates were stirred for 1 hour, collected by filtration and washed twice with 50 ml of H$_2$O. The title compound was dried under vacuum at 60° C. for 18 hours, mp 242°–244° C. (dec).

EXAMPLE 7

3-(p-Chlorophenylthiazolo[3,2-a]benzimidazole-2-acetic acid

A mixture of 3-(p-chlorophenyl)-2,3-dihydro-3-hydroxythiazolo[3,2-a]benzimidazole-2-acetic acid, hydrochloric acid salt (20 g) and orthophosphoric acid (40 g) was heated to 100° C. for 4 hours. The reaction solution was cooled to 25° C. and to this 100 ml of H$_2$O was added dropwise so as not to exceed a temperature of 60° C. After the addition was complete, the mixture was stirred at 60° C. for 1 hour. White solids were collected by filtration at 60° C., reslurried in 80 ml of hot water (60° C.) and stirred for 30 minutes at 60° C. The white solids were then removed by filtration and washed with 50 ml of H$_2$O.

To the solids in 75 ml of H$_2$O, was added 8.2 ml ammonium hydroxide to make pH of the solution 9.5. The solution was filtered through a bed of celite. To the clear solution, 4 ml of glacial acetic acid was added dropwise until pH 5.5. The precipitates were stirred for 1 hour, collected by filtration and washed twice with 50 ml of H$_2$O. The title compound was dried under vacuum at 60° C. for 18 hours. Yield 15.2 g (88.8%); mp 242°–244° C. (dec).

We claim:

1. A process for preparing a thiazolo[3,2-a]benzimidazole of formula I

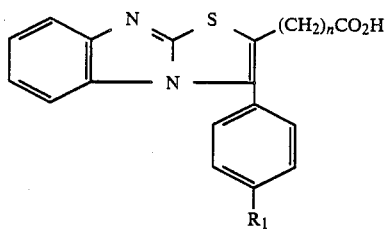

in which formula n is 1 or 2, and $R_1$ is hydrogen, lower alkyl, lower alkoxy, trifluoromethyl or halo, or a salt thereof which comprises dehydrating a compound of formula II

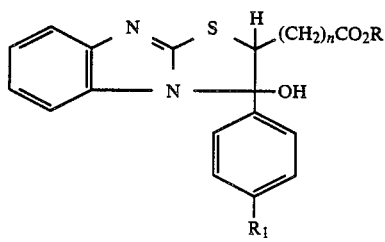

or a salt thereof wherein n and R, are as defined above, and COOR is an acid or ester function in the presence of an acid selected from sulphuric, sulphonic and phosphoric acid or mixtures thereof and if desired or required an inert solvent provided that if water is present then the amount of water is less than about 15% by volume of the acid, the reaction being carried out with heating if necessary.

2. A process according to claim 1 in which the amount of water present is less than about 10% by volume of the acid.

3. A process according to claim 1 in which the amount of water present is less than about 5% by volume of the acid.

4. A process according to claim 1 which is carried out under substantially anhydrous conditions.

5. A process according to claim 1 in which the acid is sulphuric acid.

6. A process according to claim 1 in which the acid is an alkylsulphonic acid.

7. A process according to claim 1 in which the acid is a loweralkylsulphonic acid.

8. A process according to claim 1 in which the acid is methanesulphonic acid.

9. A process according to claim 1 in which n is 1.

10. A process according to claim 1 in which R is hydrogen, $R_1$ is chlorine and n is 1.

* * * * *